United States Patent
Hashimoto et al.

(10) Patent No.: US 10,343,147 B2
(45) Date of Patent: Jul. 9, 2019

(54) METHANATION REACTION CATALYST, METHOD FOR PRODUCING METHANATION REACTION CATALYST AND METHOD FOR PRODUCING METHANE

(71) Applicant: HITACHI ZOSEN CORPORATION, Osaka (JP)

(72) Inventors: Koji Hashimoto, Miyagi (JP); Hiroyuki Takano, Chiba (JP); Kouichi Izumiya, Chiba (JP); Naokazu Kumagai, Chiba (JP)

(73) Assignee: HITACHI ZOSEN CORPORATION, Osaka (JP)

( * ) Notice: Subject to any disclaimer, the term of this patent is extended or adjusted under 35 U.S.C. 154(b) by 0 days.

(21) Appl. No.: 15/326,959

(22) PCT Filed: Jul. 16, 2015

(86) PCT No.: PCT/JP2015/070437
§ 371 (c)(1),
(2) Date: Jan. 17, 2017

(87) PCT Pub. No.: WO2016/013488
PCT Pub. Date: Jan. 28, 2016

(65) Prior Publication Data
US 2017/0209851 A1    Jul. 27, 2017

(30) Foreign Application Priority Data
Jul. 19, 2014  (JP) .................................. 2014-148373

(51) Int. Cl.
*C07C 1/12*    (2006.01)
*C07C 9/04*    (2006.01)
(Continued)

(52) U.S. Cl.
CPC .......... *B01J 23/755* (2013.01); *B01J 23/002* (2013.01); *B01J 23/02* (2013.01); *B01J 23/78* (2013.01);
(Continued)

(58) Field of Classification Search
None
See application file for complete search history.

(56) References Cited

U.S. PATENT DOCUMENTS

2009/0042998 A1    2/2009   Hashimoto et al.

FOREIGN PATENT DOCUMENTS

| CN | 102151570 A | 8/2011 |
|---|---|---|
| EP | 2033943 A1 | 3/2009 |

(Continued)

OTHER PUBLICATIONS

JP2000254508, Sep. 19, 2000, pp. 1-13; English translation (Year: 2000).*

(Continued)

*Primary Examiner* — Medhanit W Bahta
(74) *Attorney, Agent, or Firm* — Edwards Neils, LLC; Jean C. Edwards, Esq.

(57) ABSTRACT

A methanation reaction catalyst for methanation by allowing carbon dioxide to react with hydrogen, wherein the methanation reaction catalyst includes a stabilized zirconia support having a tetragonal crystal structure and in which Ca and Ni are incorporated in the crystal structure, and Ni in the metal state supported on the stabilized zirconia support, includes the following in atomic % based on metals in the element state, A) Zr composing the stabilized zirconia support: 6 to 62 atomic %, B) Ca incorporated in the crystal structure: 1 to 20 atomic %, and C) a total of Ni incorporated in the (Continued)

crystal structure and Ni supported on the stabilized zirconia support: 30 to 90 atomic %, and the atomic ratio of Ca/(Zr+Ca) is 0.14 to 0.25.

1 Claim, 5 Drawing Sheets

(51) Int. Cl.

| | | |
|---|---|---|
| B01J 23/755 | (2006.01) | |
| B01J 37/16 | (2006.01) | |
| B01J 23/78 | (2006.01) | |
| B01J 23/02 | (2006.01) | |
| B01J 35/00 | (2006.01) | |
| B01J 37/04 | (2006.01) | |
| B01J 37/08 | (2006.01) | |
| B01J 37/18 | (2006.01) | |
| B01J 23/00 | (2006.01) | |
| C07B 61/00 | (2006.01) | |
| B01J 35/02 | (2006.01) | |
| B01J 37/00 | (2006.01) | |

(52) U.S. Cl.
CPC ......... *B01J 35/002* (2013.01); *B01J 35/0006* (2013.01); *B01J 37/04* (2013.01); *B01J 37/088* (2013.01); *B01J 37/16* (2013.01); *B01J 37/18* (2013.01); *C07C 1/12* (2013.01); *B01J 35/023* (2013.01); *B01J 37/009* (2013.01); *B01J 37/0009* (2013.01); *B01J 37/0036* (2013.01); *B01J 2523/00* (2013.01); *C07B 61/00* (2013.01); *C07C 2521/06* (2013.01); *C07C 2523/02* (2013.01); *C07C 2523/755* (2013.01); *C07C 2523/78* (2013.01)

(56) References Cited

FOREIGN PATENT DOCUMENTS

| | | |
|---|---|---|
| JP | H10-043594 A | 2/1998 |
| JP | H10-244158 A | 9/1998 |
| JP | H10-263400 A | 10/1999 |
| JP | 2000-254508 A | 9/2000 |
| JP | 2009-034650 A | 2/2009 |
| JP | 2010-022944 A | 2/2010 |
| JP | 2011-206770 A | 10/2011 |
| SU | 1554962 A1 | 4/1990 |

OTHER PUBLICATIONS

Jorge D.A. Bellido et al., Effect of adding CaO to $ZrO_2$ support on nickel catalyst activity in dry reforming of methane, Applied Catalysis A: General 358, 2009, pp. 215-223, Elsevier, Amsterdam, NL.

International Preliminary Report on Patentability issued by WIPO dated Feb. 2, 2017, in connection with International Patent Application No. PCT/JP2015/070437.

International Search Report Issued in PCT/JP2015/070437 dated Sep. 8, 2015.

Written Opinion Issued in PCT/JP2015/070437 dated Sep. 8, 2015.

Hiroyuki Takano et al.; The effect of heat treatment on the performance of the Ni/ (Zr—Sm oxide) catalysts for carbon dioxide methanation; Applied Surface Science; Jul. 15, 2011; pp. 8171-8176; vol. 257, No. 19; Elsevier B.V.

* cited by examiner

METHANATION REACTION CATALYST, METHOD FOR PRODUCING METHANATION REACTION CATALYST AND METHOD FOR PRODUCING METHANE

CROSS-REFERENCE TO RELATED APPLICATIONS

The present application is a 35 U.S.C. 371 National Stage Entry of PCT/JP2015/070437, filed on Jul. 16, 2015, which claims priority from Japanese Patent Application 2014-148373, filed on Jul. 19, 2014, the contents of all of which are herein incorporated by reference in their entirety.

TECHNICAL FIELD

The present invention relates to a methanation reaction catalyst, a method for producing a methanation reaction catalyst, and a method for producing methane.

BACKGROUND ART

Effective use of methane that has been produced by methanation by allowing carbon dioxide to react with hydrogen has been examined Patent Documents 1 to 3 have proposed, as a catalyst used for such a methanation reaction of carbon dioxide, for example, an amorphous alloy catalyst ribbon produced by melting an alloy of iron group metals such as Ni and Co, and valve metal such as Zr, Ti, Nb, and Ta, and thereafter solidifying the melt by melt-quenching.

Such an amorphous alloy catalyst allows efficient conversion of carbon dioxide to methane, and has a high conversion ratio from carbon dioxide to methane. However, because it is produced by melt-quenching, it is not suitable for mass production, and because it is a ribbon type, disadvantages are that applicable reactors (reaction system) are limited.

Thus, a powder methanation reaction catalyst that is highly mass productive, and is widely applicable to various reactors (reaction systems) is desired.

Patent Document 4 has proposed, for such a powder methanation reaction catalyst, for example, a carbon dioxide methanation catalyst prepared by immersing a tetragonal zirconia support in an aqueous solution of salt of Ni and/or Co, and then drying and calcining the mixture, and then, reducing the calcined product: the tetragonal zirconia support including one or two stabilizing element selected from the group consisting of Y, La, Ce, Pr, Nd, Sm, Gd, Tb, Dy, Eu, Mg, and Ca.

Furthermore, improvement in carbon dioxide conversion ratio of the powder methanation reaction catalyst has been examined.

For example, Patent Document 5 has proposed a methanation reaction catalyst prepared by mixing zirconia hydrosol, an aqueous solution of a salt of a stabilizing element, and an aqueous solution of a salt of an iron group element, and then drying and calcining the mixture, and then, reducing the calcined product. In the methanation reaction catalyst, a portion of an iron group element is incorporated into the tetragonal zirconia support along with a stabilizing element, and the metal state iron group element is supported on the tetragonal zirconia support.

CITATION LIST

Patent Document

Patent Document 1: Japanese Unexamined Patent Publication No. H 10-043594
Patent Document 2: Japanese Unexamined Patent Publication No. H10-244158
Patent Document 3: Japanese Unexamined Patent Publication No. H10-263400
Patent Document 4: Japanese Unexamined Patent Publication No. 2000-254508
Patent Document 5: Japanese Unexamined Patent Publication No. 2010-022944

SUMMARY OF THE INVENTION

Problem to be Solved by the Invention

However, in the methanation reaction catalyst described in Patent Document 5, improvement in conversion ratio (hereinafter referred to as carbon dioxide conversion ratio) from carbon dioxide to methane may not be sufficiently achieved.

An object of the present invention is to provide a methanation reaction catalyst with which carbon dioxide conversion ratio can be improved, a method for producing a methanation reaction catalyst, and a method for producing methane.

Means for Solving the Problem

[1] The present invention relates to a methanation reaction catalyst for methanation by allowing carbon dioxide to react with hydrogen,
wherein the methanation reaction catalyst includes a stabilized zirconia support having a tetragonal crystal structure and in which Ca and Ni are incorporated in the crystal structure, and Ni in the metal state supported on the stabilized zirconia support;
the methanation reaction catalyst includes the following in atomic % based on the metals in the element state,
A) Zr composing the stabilized zirconia support: 6 to 62 atomic %,
B) Ca incorporated in the crystal structure: 1 to 20 atomic %, and
C) a total of Ni incorporated in the crystal structure and Ni supported on the stabilized zirconia support: 30 to 90 atomic %, and
the atomic ratio of Ca/(Zr+Ca) is 0.14 to 0.25.

[2] The present invention includes the methanation reaction catalyst of the above-described [1], wherein a total of the Ni incorporated in the crystal structure and the Ni supported on the stabilized zirconia support is 50 to 80 atomic %.

[3] The present invention includes the methanation reaction catalyst of the above-described [1] or [2], wherein the atomic ratio of (Ca+Ni)/(Zr+Ca+Ni) is 0.55 to 0.90.

[4] The present invention includes a method for producing a methanation reaction catalyst, the method including:
preparing a mixture by mixing zirconia and/or a Zr salt, a Ca salt, a Ni salt, so that based on the metals in the element state, the following atomic percent is achieved:
Zr: 6 to 62 atomic %, Ca: 1 to 20 atomic %, and Ni: 30 to 90 atomic %, and that the atomic ratio of Ca/(Zr+Ca) is 0.14 to 0.25;
calcining the mixture at 500 to 800° C., and then reducing the calcined product.

[5] The present invention includes a method for producing methane, wherein any one of the methanation reaction catalyst of the above-described [1] to [3] is allowed to contact with a gas mixture containing at least carbon dioxide and hydrogen gas under the condition of 300 to 400° C.

Effects of the Invention

The methanation reaction catalyst of the present invention has an atomic ratio of Ca/(Zr+Ca) of 0.14 to 0.25, and therefore the carbon dioxide conversion ratio can be improved. Furthermore, Ca, which is low-cost compared with rare-earth elements such as Y and La, is incorporated in the crystal structure of the stabilized zirconia support along with Ni to stabilize the crystal structure, and therefore compared with the case where rare-earth elements are selected as the stabilizing element, reduction in raw material costs can be achieved.

That is, the methanation reaction catalyst of the present invention allows reduction in raw material costs, and achieves improvement in carbon dioxide conversion ratio.

In the method for producing a methanation reaction catalyst of the present invention, the above-described methanation reaction catalyst can be produced by preparing a mixture by mixing zirconia and/or a Zr salt, a Ca salt, and a Ni salt, so that based on the metals in the element state, the atomic % of Zr, Ca, and Ni is in a predetermined range, and that the atomic ratio of Ca/(Zr+Ca) is in a predetermined range; drying the mixture; calcining the mixture at 500 to 800° C.; and then reducing the calcined product.

Therefore, the methanation reaction catalyst that allows for improvement in carbon dioxide conversion ratio can be produced with an easy method.

With the method for producing methane of the present invention, the above-described methanation reaction catalyst is allowed to contact with a gas mixture containing at least carbon dioxide and hydrogen gas under the condition of 300 to 400° C., and therefore carbon dioxide can be converted efficiently to methane, and methane can be produced efficiently.

DESCRIPTION OF EMBODIMENTS

1. Methanation Reaction Catalyst

A methanation reaction catalyst is a catalyst for allowing carbon dioxide to react with hydrogen for methanation, and includes a stabilized zirconia support, and Ni in the metal state supported on the stabilized zirconia support.

The stabilized zirconia support has a tetragonal crystal structure composed mainly of Zr, and Ca and Ni are incorporated in its crystal structure.

Figure 1:
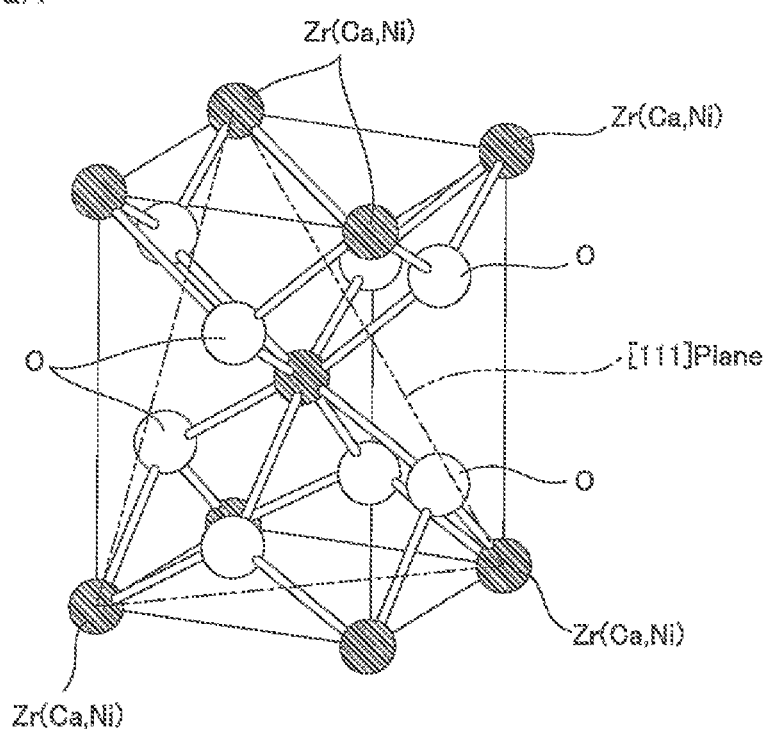
FIG. 1 is a diagram for illustrating a crystal structure of a stabilized zirconia support according to the methanation reaction catalyst of the present invention.

To be more specific, the stabilized zirconia support has a tetragonal system composed mainly of Zr, and preferably, as shown in FIG. 1, has a body-centered tetragonal zirconia crystal structure. That is, the crystal structure of the stabilized zirconia support is composed with Zr as a main component (fundamental component), and mainly Zr ions ($Zr^{4+}$) are disposed at a plurality of lattice points of the crystal structure of the stabilized zirconia support.

Furthermore, Ca and Ni are incorporated in the crystal structure of the stabilized zirconia support, and the crystal structure of the tetragonal system is stabilized.

"Ca and Ni are incorporated in the crystal structure of the stabilized zirconia support" means that at a part of the lattice points out of the plurality of lattice points of the crystal structure, Zr ion ($Zr^{4+}$) is replaced with any of Ca ion ($Ca^{2+}$) and Ni ion ($Ni^{2+}$). That is, incorporation of Ca into the crystal structure means that the Zr ion disposed at the lattice point of the crystal structure is replaced with Ca ion, and incorporation of Ni into the crystal structure means that the Zr ion disposed at the lattice point of the crystal structure is replaced with Ni ion.

Therefore, at the plurality of lattice points of the stabilized zirconia support, any one of $Zr^{4+}$, $Ca^{2+}$, and $Ni^{2+}$ is disposed.

Such a stabilized zirconia support is represented by the general formula (1) below: General formula (1):

$$Zr^{4+}_{1-(x+y)}Ca^{2+}_{x}Ni^{2+}_{y}O_{2-(x+y)} \quad (1)$$

(in the general formula (1), x and y are less than 1, and x+y is less than 1)

In the general formula (1), x is, for example, 0.133 or more, and less than 1, preferably 0.248 or less.

In the general formula (1), y is, for example, 0.010 or more, and less than 1, preferably 0.050 or less.

Furthermore, the crystal lattice spacing in the stabilized zirconia support changes depending on the amounts of Ca and Ni incorporated in the crystal structure, because the ionic radius of $Zr^{4+}$, $Ca^{2+}$, and $Ni^{2+}$ is different, as shown below.

$Zr^{4+}$: 0.079 nm
$Ca^{2+}$: 0.099 nm
$Ni^{2+}$: 0.069 nm

To be more specific, when Ca ions, which have a larger ionic radius than that of Zr ions, are incorporated more in the crystal structure (that is, when x increases in the general formula (1)), the crystal lattice spacing in the stabilized zirconia support increases (expands). Meanwhile, when Ni ions, which have a smaller ionic radius than that of Zr ions, are incorporated more in the crystal structure (that is, when y increases in the general formula (1)), the crystal lattice spacing in the stabilized zirconia support decreases (shrinks).

The lattice spacing of the [111] planes (shown in the phantom line in FIG. 1) of the crystal structure of the stabilized zirconia support is, for example, 0.2940 nm or more, preferably 0.2945 nm or more, and for example, 0.2965 nm or less, preferably 0.2960 nm or less.

Furthermore, when Ca and Ni are incorporated in the crystal structure of the stabilized zirconia support, because Zr ion ($Zr^{4+}$) is quadrivalent, and Ca ion ($Ca^{2+}$) and Ni ion ($Ni^{2+}$) are divalent, oxygen defect (deficiency) is caused, and oxygen void is formed in the crystal structure.

That is, the general formula (2) below represents the above-described the general formula (1) representing the stabilized zirconia support including the oxygen void "Vo" formed therein.

General Formula (2):

$$Zr^{4+}{}_{1-(x+y)}Ca^{2+}{}_{x}Ni^{2+}{}_{y}O_{2-(x+y)}Vo_{x+y} \quad (2)$$

(in the general formula (2), x and y represent the same range as those of x and y in the above-described general formula (1))

In the methanation reaction catalyst, Ni in the metal state is supported on the above-described stabilized zirconia support.

Therefore, the methanation reaction catalyst is represented by the general formula (3) below.

General Formula (3):

$$Ni/Zr^{4+}{}_{1-(x+y)}Ca^{2+}{}_{x}Ni^{2+}{}_{y}O_{2-(x+y)}Vo_{x+y} \quad (3)$$

(in the general formula (3), x and y represent the same range as x and y of the above-described general formula (1))

That is, the methanation reaction catalyst contains Zr composing the stabilized zirconia support, Ca incorporated in the crystal structure of the stabilized zirconia support, Ni incorporated in the crystal structure of the stabilized zirconia support, and Ni supported on the stabilized zirconia support.

In the methanation reaction catalyst, based on atomic % of the metals in the element state, The atomic % of Zr is 6 atomic % or more, preferably 7 atomic % or more, more preferably 15 atomic % or more, and 62 atomic % or less, preferably 60 atomic % or less, more preferably 50 atomic % or less. The atomic % of the atoms in the methanation reaction catalyst is converted from the amount of the material charged (zirconia and/or Zr salt, Ca salt, Ni salt) used in the method for producing a methanation reaction catalyst described later.

When the atomic % of Zr is the above-described lower limit or more, the tetragonal crystal structure can be reliably formed in the stabilized zirconia support, and when the atomic % of Zr is the above-described upper limit or less, the atomic % of Ni that is necessary for the catalytic activity can be ensured sufficiently.

In the methanation reaction catalyst, based on atomic % of the metals in the element state, atomic % of Ca is 1 atomic % or more, preferably 1.4 atomic % or more, more preferably 2.6 atomic % or more, and 20 atomic % or less, preferably 18 atomic % or less, more preferably 10 atomic % or less.

When the atomic % of Ca is the above-described lower limit or more, the tetragonal crystal structure can be stabilized reliably, and when the atomic % of Ca is the above-described upper limit or less, hindrance to catalytic activity from excessive Ca forming undesired oxide (e.g., $CaZrO_3$, etc.) can be suppressed.

In the methanation reaction catalyst, based on atomic % of the metals in the element state, a total atomic % of the Ni incorporated in the crystal structure and Ni supported on the stabilized zirconia support (hereinafter a total of Ni) is 30 atomic % or more, preferably 50 atomic % or more, more preferably 55 atomic % or more, and 90 atomic % or less, preferably 80 atomic % or less, more preferably 75 atomic % or less.

When the total atomic % of Ni is the above-described lower limit or more, catalytic activity can be improved, and when the total atomic % of Ni is the above-described upper limit or less, reduction of Ni dispersiveness by Ni coagulation can be suppressed.

In the methanation reaction catalyst, the atomic ratio of Ca/(Zr+Ca) is 0.14 or more, preferably 0.15 or more, more preferably 0.165 or more, and 0.25 or less, preferably 0.22 or less, more preferably 0.20 or less.

When the atomic ratio of Ca/(Zr+Ca) is the above-described lower limit or more and is the above-described upper limit or less, oxygen void can be excellently formed in the stabilized zirconia support (ref: the above-described general formula (2)), and in the method for producing methane described later, the stabilized zirconia support can attract oxygen atom (O) of carbon dioxide molecule ($CO_2$). Therefore, catalytic activity can be improved reliably, and carbon dioxide to methane conversion ratio (hereinafter referred to as $CO_2$ conversion ratio %) can be improved.

In particular, when the total Ni atomic % is 50 atomic % or more and 80 atomic % or less and the atomic ratio of Ca/(Zr+Ca) is 0.15 or more and 0.22 or less, the $CO_2$ conversion ratio % can be improved more reliably (e.g., $CO_2$ conversion ratio % is 80% or more), and when the total Ni atomic % is 55 atomic % or more and 75 atomic % or less and the atomic ratio of Ca/(Zr+Ca) is 0.15 or more and 0.22 or less, the $CO_2$ conversion ratio % can be improved even more (e.g., $CO_2$ conversion ratio % is 90% or more).

In the methanation reaction catalyst, the atomic ratio of (Ca+Ni)/(Zr+Ca+Ni) is, for example, 0.400 or more, preferably 0.550 or more, more preferably 0.740 or more, and for example, 0.925 or less, preferably 0.900 or less, more preferably 0.780 or less.

When the atomic ratio of (Ca+Ni)/(Zr+Ca+Ni) is the above-described lower limit or more and is the above-described upper limit or less, oxygen void can be excellently formed in the stabilized zirconia support (ref; the above-described general formula (2)), and in the method for producing methane described later, the stabilized zirconia support can reliably attract the oxygen atom (O) of the carbon dioxide molecule ($CO_2$).

In the methanation reaction catalyst, as necessary, a dilution component, a particulate component, and a binder can be added.

The dilution component is a substance that is inert to the methanation reaction described later, and by adding the dilution component to the methanation reaction catalyst, the temperature control for the methanation reaction catalyst can be made easy.

Examples of the dilution component include alumina (e.g., α-alumina, θ-alumina, γ-alumina, etc.), and preferably, α-alumina is used. Such a dilution component can be used singly, or can be used in combination of two or more.

The dilution component can be added in an amount of, relative to 100 parts by mass of the methanation reaction catalyst, for example, 100 parts by mass or more, preferably 1000 parts by mass or more, for example, 10000 parts by mass or less, preferably 5000 parts by mass or less.

Examples of the particulate component include alumina (e.g., α-alumina, θ-alumina, γ-alumina, etc.), silica, and titania, preferably, alumina, even more preferably, γ-alumina is used. The particulate component can be used singly, or can be used in combination of two or more.

Examples of the binder include silicate, titanate, aluminate, and zirconate. The binder can be used singly, or can be used in combination of two or more.

2. Method for Producing a Methanation Reaction Catalyst

Next, description is given below of an embodiment of the method for producing a methanation reaction catalyst.

To produce the methanation reaction catalyst, for example, first, a mixture is prepared by mixing, as materials, zirconia ($ZrO_2$) and/or a Zr salt, a Ca salt, and a Ni salt so that based on the metals in the element state, the following atomic % is achieved, Zr: 6 to 62 atomic %, Ca: 1 to 20 atomic %, Ni: 30 to 90 atomic %, and that the atomic ratio of Ca/(Zr+Ca) is 0.14 to 0.25.

Examples of the Zr salts include Zr nitrate (e.g., zirconium nitrate ($Zr(NO_3)_4$), zirconium nitrate oxide ($ZrO(NO_3)_2$), etc.), Zr hydrochloride (e.g., zirconium chloride oxide ($ZrCl_2O$), etc.), and Zr acetate (e.g., zirconium acetate oxide ($ZrO(C_2H_3O_2)_2$), etc.). Zr salts can be used singly, or can be used in combination of two or more.

For the Zr salts, a commercially available product can be used, and examples of the commercially available product include zirconium nitrate pentahydrite (manufactured by BOC sciences), zirconium nitrate oxide dihydrate (manufactured by KANTO CHEMICAL CO., INC.), and zirconium chloride oxide octahydrate (manufactured by KANTO CHEMICAL CO., INC.).

Of zirconia and Zr salts, preferably, zirconia is used.

Examples of the Ca salts include Ca nitrate (e.g., calcium nitrate ($Ca(NO_3)_2$), etc.) and Ca chloride (e.g., calcium chloride ($CaCl_2$), etc.). The Ca salts can be used singly, or can be used in combination of two or more.

Of the Ca salts, preferably, Ca nitrate is used, even more preferably, calcium nitrate is used.

Examples of the Ni salt include Ni nitrate (e.g., nickel nitrate ($Ni(NO_3)_2$), etc.) and Ni chloride (e.g., nickel chloride ($NiCl_2$), etc.). The Ni salt can be used singly, or can be used in combination of two or more.

Of the Ni salts, preferably, nitric acid salts are used, even more preferably, nickel nitrate is used.

To mix the zirconia and/or a Zr salt, a Ca salt, and a Ni salt, for example, a zirconia hydrosol and/or an aqueous solution of a Zr salt, an aqueous solution of a Ca salt, and an aqueous solution of a Ni salt are mixed so that the atomic % of the atoms (Zr, Ca, and Ni) is in the above-described range, and the atomic ratio of Ca/(Zr+Ca) is in the above-described range, and the mixture is stirred.

To be more specific, the zirconia hydrosol and/or the aqueous solution of a Zr salt are mixed and stirred with the aqueous solution of a Ca salt for, for example, 1 hour or more and 30 hours or less to prepare a homogeneous solution. Then, the aqueous solution of Ni salt is added thereto, and the mixture is mixed and stirred, for example, for 1 hour or more and 30 hours or less.

A mixture solution containing zirconia and/or a Zr salt, a Ca salt, and a Ni salt is prepared in this manner Then, after the mixture solution is allowed to stand for, for example, 30 minutes or more and 3 hours or less, the mixture solution is evaporated to dryness with, for example, a heating furnace such as a muffle furnace.

The mixture solution is dried at a temperature of, for example, 100° C. or more, preferably 150° C. or more, and for example, 300° C. or less, preferably 200° C. or less. The mixture solution is dried for, for example, 30 minutes or more, preferably 1 hour or more, and for example, 10 hours or less, preferably 3 hours or less.

In this manner, the moisture component is removed from the mixture solution, and a mixture in which zirconia and/or a Zr salt, a Ca salt, and a Ni salt are homogenously mixed is prepared in this manner Then, the mixture is calcined with, for example, a heating furnace such as a muffle furnace.

The calcining is performed at a temperature of, 500° C. or more, preferably 600° C. or more, and 800° C. or less.

When the calcining temperature is the above-described lower limit or more and is the above-described upper limit or less, the crystal structure of the stabilized zirconia support can be reliably made into a tetragonal system.

The calcining time is, for example, 1 hour or more, preferably 3 hours or more, and for example, 10 hours or less, preferably 7 hours or less.

In this manner, the mixture is calcined; the stabilized zirconia support represented by the above-described general formula (1) is formed; nickel oxide is supported on the stabilized zirconia support; and a catalyst precursor represented by the general formula (4) below is prepared.

General Formula (4):

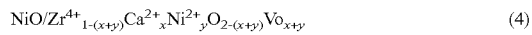

$$NiO/Zr^{4+}_{1-(x+y)}Ca^{2+}_{x}Ni^{2+}_{y}O_{2-(x+y)}Vo_{x+y} \quad (4)$$

(in the general formula (4), x and y represent the same range as x and y of the above-described general formula (1))

That is, Ca and Ni are incorporated into the crystal structure of the stabilized zirconia support, and nickel oxide is supported on the stabilized zirconia support.

Then, as necessary, the catalyst precursor is ground with a mortar and sieved, and then reduced under hydrogen flow.

The reducing temperature is, for example, 200° C. or more, preferably 300° C. or more, and for example, 600° C. or less, preferably 500° C. or less. The reducing time is, for example, 1 hour or more, preferably 3 hours or more, and for example, 10 hours or less, preferably 7 hours or less.

In the above-described manner, the nickel oxide supported on the stabilized zirconia support is reduced, thereby preparing the methanation reaction catalyst represented by the above-described general formula (3).

Zr, Ca, and Ni contained in the stabilized zirconia support are covered with the nickel oxide supported on the stabilized zirconia support, and therefore they are not reduced in this reduction step, and their oxidized status is kept.

When a dilution component is added to the methanation reaction catalyst, the methanation reaction catalyst and the dilution component are mixed with the above-described ratio, and then can be subjected to reduction treatment.

When a particulate component and/or a binder is added to the methanation reaction catalyst, after the particulate component and/or binder is added to the above-described mixture solution, the mixture solution can be evaporated to dryness, and then can be calcined. The particulate catalyst precursor with a maximum diameter of 3 mm can be formed in this manner After the particulate component and/or binder is added and mixed to the methanation reaction catalyst, and then the mixture can be heated to be calcined again.

3. Method for Producing Methane

Next, description is given below of the method for producing methane using the above-described methanation reaction catalyst.

To produce methane with the methanation reaction catalyst, the methanation reaction catalyst is allowed to contact with a gas mixture containing at least carbon dioxide and hydrogen gas under conditions of the following: under normal pressure at 300° C. or more, preferably 350° C. or less, 400° C. or less.

The gas mixture is not particularly limited, as long as at least carbon dioxide and hydrogen gas are contained, and carbon monoxide and nitrogen may be contained as other gases. That is, examples of the gas mixture include a gas mixture of carbon dioxide and hydrogen, a gas mixture of carbon monoxide, carbon dioxide, and hydrogen, and a gas mixture mainly containing these. In the gas mixture, the molar ratio of carbon dioxide to hydrogen gas is 1:4.

The gas mixture flow rate is, for example, 20 L/hour or more, preferably 50 L/hour or more, and for example, 100 L/hour or less, preferably 70 L/hour or less.

By allowing the methanation reaction catalyst to contact with the gas mixture, the oxygen void of the methanation reaction catalyst attracts the oxygen atom of carbon dioxide, and therefore chemical reaction of the chemical formula (5) below progresses at the surface of the methanation reaction catalyst, and carbon dioxide is allowed to react with hydrogen efficiently, thereby producing methane.

Chemical Formula (5):
[Chem. 1]

$$CO_2 + 4H_2 \leftrightarrows CH_4 + 2H_2O \tag{5}$$

The chemical reaction shown in the above-described chemical formula (5) allows, by removing water produced along with methane, under normal pressure, to tilt the equilibrium to the product side (methane side), and methane can be produced efficiently with simple facilities.

When the gas mixture contains carbon monoxide, the methanation reaction catalyst converts, first, all of the carbon monoxide to methane, and then converts the carbon dioxide to methane. Therefore, carbon monoxide can be removed reliably.

In such a method for producing methane, metal Ni supported on the surface of the methanation reaction catalyst may be detached and separated from the methanation reaction catalyst by supply of the gas mixture. In this case, Ni ion of the stabilized zirconia support exposed from the detached portion is reduced to be in a meal state by being reduced by hydrogen in the gas mixture, and works as catalytic activity points, and therefore the methanation reaction catalyst can ensure catalytic activity sufficiently.

4. Operations and Effects

The methanation reaction catalyst has an atomic ratio of Ca/(Zr+Ca) of 0.14 to 0.25, and therefore the conversion ratio of carbon dioxide can be improved. Furthermore, Ca, which is low cost compared with rare-earth elements, is incorporated in the crystal structure of the stabilized zirconia support along with Ni, and stabilizes its crystal structure, and therefore reduction in raw material costs can be achieved. That is, the methanation reaction catalyst can achieve reduction in raw material costs, and can improve conversion ratio of carbon dioxide.

In the method for producing a methanation reaction catalyst, the above-described methanation reaction catalyst can be produced by the following: preparing a mixture by mixing zirconia and/or a Zr salt, a Ca salt, and a Ni salt so that atomic % of Zr, Ca, and Ni based on the metals in the element state is in a predetermined range and the atomic ratio of Ca/(Zr+Ca) is in a predetermined range; drying the mixture; calcining the mixture at 500 to 800° C.; and then reducing the calcined product.

Therefore, the methanation reaction catalyst that allows for improvement in carbon dioxide conversion ratio can be produced with an easy method.

In the method for producing methane, the above-described methanation reaction catalyst is allowed to contact with the gas mixture containing at least carbon dioxide and hydrogen gas under condition of 300 to 400° C., and therefore carbon dioxide can be converted to methane efficiently, and methane can be produced efficiently.

The methanation reaction catalyst includes the stabilized zirconia support having a tetragonal crystal structure, but may include, partially, zirconia having a monoclinic crystal structure (monoclinic crystal zirconia).

EXAMPLES

In the following, the present invention is described in further detail with reference to Examples. However, the present invention is not limited to these. The specific numeral values such as mixing ratio (content), physical property values, and parameters used in the description below can be replaced with the upper limit value (numeral values defined with "or less", "less than") or the lower limit value (numeral values defined with "or more", "more than") of the corresponding mixing ratio (content), physical property values, parameters in the above-described "DESCRIPTION OF EMBODIMENTS".

Examples 1 to 20 and Comparative Examples 1 to 10

To zirconia (zirconium dioxide, oxide of Zr) hydrosol (trade name: "Zr 30AH", manufactured by Nissan Chemical Industries, Ltd., Zr: 30 mass %, pH=4.0), an aqueous solution of calcium nitrate, in which calcium nitrate tetrahydrate (Ca salt) was dissolved in pure water was added so that the composition (atomic % of Zr and Ca and atomic ratio of Ca/(Zr+Ca)) shown in Table 1 to Table 3 was achieved, and the mixture was stirred, thereby preparing a homogeneous white solution.

Then, to the white solution, an aqueous solution of nickel nitrate in which nickel nitrate hexahydrate (Ni salt) is dissolved in pure water was added to achieve the composition (atomic % of Ni) shown in Table 1 to Table 3, and the mixture was stirred for 24 hours, thereby preparing a homogeneous mixture solution.

Then, the mixture solution was allowed to stand for 1 hour, and then the mixture was put into a muffle furnace and kept at 170° C. for 2 hours to remove moisture component and dry the mixture, thereby preparing a mixture of zirconia, calcium nitrate, and nickel nitrate. Then, the mixture was calcined at 650° C. for 5 hours, thereby preparing a gray catalyst precursor.

Then, the catalyst precursor was ground with an agate mortar, put through a sieve with 100 μm mesh, and those passed through were collected.

Then, 0.15 g of the catalyst precursor that was passed through was mixed with 8.75 g of α-alumina (aluminum oxide, dilution component) to prepare an alumina added catalyst precursor, and the alumina added catalyst precursor was disposed in a quartz tube (reaction tube) with a size of internal diameter 15 mm×length 50 mm, and fixed with quartz wool. The alumina added catalyst precursor was put in an amount of about 10 cm³.

Then, the reaction tube was put into the electric furnace, and a thermocouple was put into the reaction tube, thereby allowing contact with the alumina added catalyst precursor. Then, heating was conducted so that the temperature of the thermocouple was 400° C., and reduction was performed under hydrogen flow for 5 hours, thereby producing an alumina-added methanation reaction catalyst.

The methanation reaction catalyst included a stabilized zirconia support, and Ni in the metal state supported on the stabilized zirconia support.

Examples 21 to 24 and Comparative Examples 11 and 12

A methanation reaction catalyst was produced in the same manner as described above, except that the calcining temperature of the mixture was changed from 650° C. to 800° C.

Measurement and Evaluation)

1) Crystal Lattice Spacing Between [111] Planes in Stabilized Zirconia Support

For the methanation reaction catalyst of Examples 5 to 12, 21 to 24, and Comparative Examples 3 to 6, 11, and 12, the crystal lattice spacing in the [111] planes of the stabilized zirconia support was calculated using the Bragg's formula based on the angle for 111 diffraction ray obtained by powder X-ray diffraction method. The results are shown in Tables 1, 2, 4 and FIG. 2. In Tables 1, 2, and 4, the stabilized zirconia support was Zr support, and in FIG. 2, atomic % is shown as atomic %.

Figure 2:
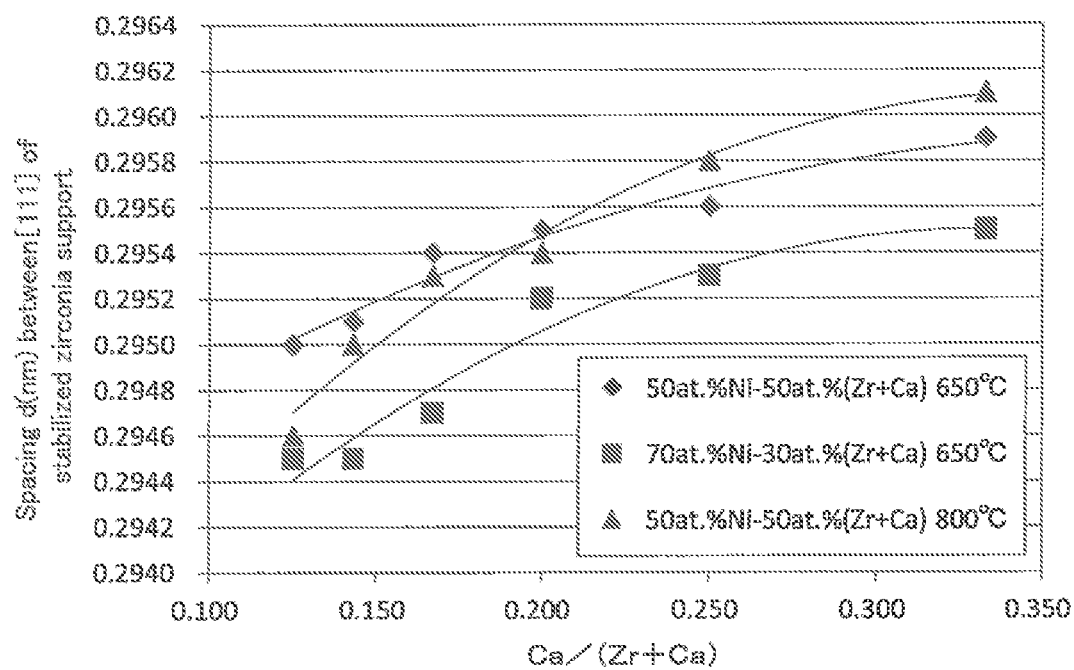
FIG. 2 is a graph illustrating correlation between the crystal lattice spacing of the [111] planes of the stabilized zirconia support relative to the atomic ratio of Ca/(Zr+Ca) in Examples 5 to 12, 21 to 24 and Comparative Examples 3 to 6, 11, and 12 according to the methanation reaction catalyst of the present invention.

In FIG. 2, it was confirmed that as the atomic ratio of Ca/(Zr+Ca) increases, the crystal lattice spacing in the [111] planes of the stabilized zirconia support increases (expands), and as the atomic % of Ni increases, the crystal lattice spacing in the [111] planes of the stabilized zirconia support decreases (shrinks).

2) X-Ray Diffraction

The catalyst component of the methanation reaction catalyst of Examples 5 to 8, Comparative Example 3 and Comparative Example 4 was analyzed with X-ray diffraction (glancing angle 10°, Cu-Kα). The results are shown in FIG. 3.

The catalyst component of the methanation reaction catalyst of Examples 21 to 24, Comparative Example 11 and 12 was analyzed with X-ray diffraction (glancing angle 10°, Cu-Kα). The results are shown in FIG. 4.

Figure 3:
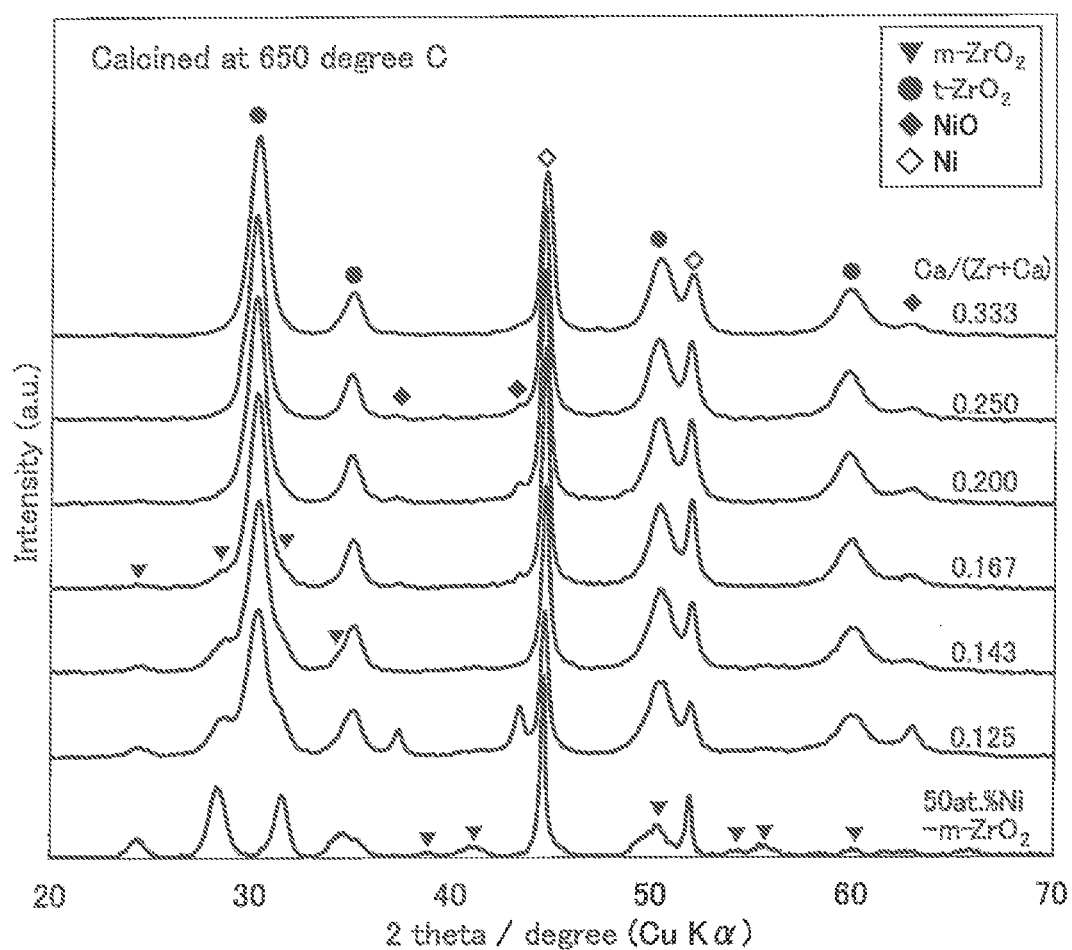
FIG. 3 is an X-ray diffraction chart for Examples 5 to 8 and Comparative Examples 3 and 4 according to the methanation reaction catalyst of the present invention.
Figure 4:
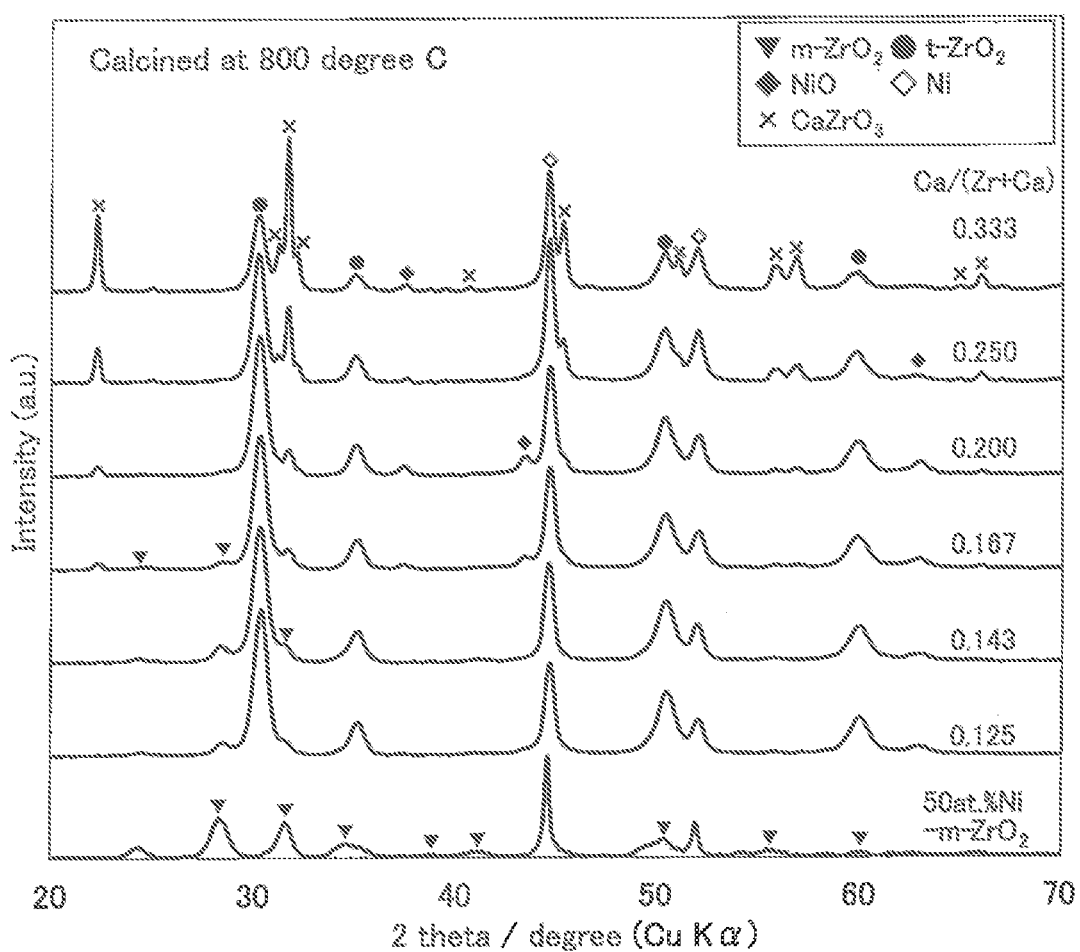
FIG. 4 is an X-ray diffraction chart for Examples 21 to 24 and Comparative Examples 11 and 12 according to the methanation reaction catalyst of the present invention.

In FIG. 3 and FIG. 4, zirconia having a tetragonal crystal structure is shown as $t\text{-}ZrO_2$, and zirconia having a monoclinic crystal structure is shown as $m\text{-}ZrO_2$.

In FIG. 3 and FIG. 4, it was confirmed that the main component of the methanation reaction catalyst was zirconia having a tetragonal crystal structure (tetragonal zirconia) and Ni in the metal state. In the methanation reaction catalyst, a small amount of zirconia having a monoclinic crystal structure (monoclinic zirconia) was produced, but the presence of Ca stabilized the tetragonal zirconia. The non-reduced nickel oxide NiO was incorporated inside the stabilized zirconia support.

3) Conversion Ratio of Carbon Dioxide to Methane ($CO_2$ Conversion Ratio %)

The methanation reaction catalyst of Examples 1 to 20 and Comparative Examples 1 to 10 was kept at 300° C., 350° C., or 400° C. (reaction temperature), and material gas (gas mixture) containing carbon dioxide, hydrogen, and nitrogen was supplied in a reaction tube, thereby allowing contact with the methanation reaction catalyst.

In the material gas, the molar ratio of carbon dioxide to hydrogen was 1:4, and nitrogen was 5% by volume. The flow rate of the material gas was 60 L/hour, and was 400 L/(hour·g) relative to 1 g of the catalyst component.

After contacting with the methanation reaction catalyst, the reaction gas flew out of the reaction tube was analyzed with a thermal conductivity detector (TCD) gas chromatograph. The reaction gas contained only unreacted hydrogen, unreacted carbon dioxide, and product methane, and reaction selectivity to methane was 100%.

The conversion ratio ($CO_2$ conversion ratio %) of carbon dioxide to methane was obtained based on the ratio of the amounts of hydrogen and carbon dioxide of the material gas introduced in the reaction tube relative to the amounts of unreacted hydrogen and carbon dioxide in the reaction gas.

Figure 5:
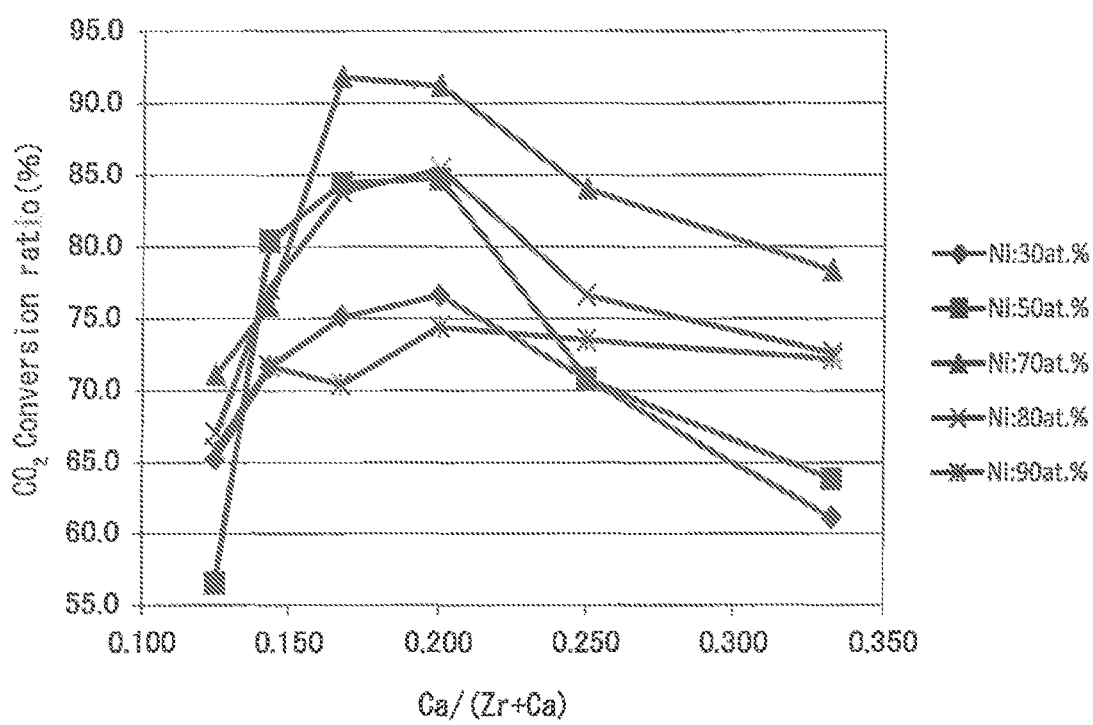
FIG. 5 is a graph illustrating correlation between the conversion ratio of the carbon dioxide to methane relative to the atomic ratio of Ca/(Zr+Ca) of Examples and Comparative Examples of the present invention according to the methanation reaction catalyst.

The results are shown in Table 1 to Table 3 and shown in FIG. 5. FIG. 5 shows the $CO_2$ conversion ratio % when the reaction temperature is 350° C., and atomic % is shown as atomic %.

In FIG. 5, it was confirmed that the $CO_2$ conversion ratio % improved when the atomic ratio of Ca/(Zr+Ca) in the methanation reaction catalyst was in the range of 0.14 to 0.25.

Also, it was confirmed that the $CO_2$ conversion ratio % improved even more when the atomic % of Ni in the methanation reaction catalyst was 50 to 80 atomic %.

It was also confirmed that the $CO_2$ conversion ratio % was more than 80% when the atomic % of Ni was 50 to 80 atomic %, and the atomic ratio of Ca/(Zr+Ca) was in the range of 0.15 to 0.22.

It was confirmed that the $CO_2$ conversion ratio % was more than 90% when the atomic % of Ni was 70 atomic %, and the atomic ratio of Ca/(Zr+Ca) was in the range of 0.165 to 0.20.

TABLE 1

| | | Comp. Ex. 1 | Ex. 1 | Ex. 2 | Ex. 3 | Ex. 4 | Comp. Ex. 2 | Comp. Ex. 3 | Ex. 5 | Ex. 6 | Ex. 7 | Ex. 8 | Comp. Ex. 4 |
|---|---|---|---|---|---|---|---|---|---|---|---|---|---|
| Composition of metallic element in catalyst | Ni (atomic %) | 30 | 30 | 30 | 30 | 30 | 30 | 50 | 50 | 50 | 50 | 50 | 50 |
| | Zr (atomic %) | 61.3 | 60.0 | 58.3 | 56.0 | 52.5 | 46.7 | 43.8 | 42.9 | 41.7 | 40.0 | 37.5 | 33.4 |
| | Ca (atomic %) | 8.8 | 10.0 | 11.7 | 14.0 | 17.5 | 23.3 | 6.3 | 7.2 | 8.4 | 10.0 | 12.5 | 16.7 |
| | Zr + Ca (atomic %) | 70 | 70 | 70 | 70 | 70 | 70 | 50 | 50 | 50 | 50 | 50 | 50 |
| | Ca/(Zr + Ca) | 0.125 | 0.143 | 0.167 | 0.200 | 0.250 | 0.333 | 0.125 | 0.143 | 0.167 | 0.200 | 0.250 | 0.333 |
| Lattice spacing d(nm) between [111] planes of Zr support | | — | — | — | — | — | — | 0.2950 | 0.2951 | 0.2954 | 0.2955 | 0.2956 | 0.2959 |
| $CO_2$ conversion ratio(%) | 300° C. | — | — | — | — | — | — | 6.5 | 22.1 | 37.5 | 47.1 | 33.4 | 23.2 |
| | 350° C. | 65.2 | 71.6 | 75.1 | 76.6 | 70.8 | 61.1 | 56.5 | 80.4 | 84.4 | 84.7 | 70.8 | 63.8 |
| | 400° C. | — | — | — | — | — | — | 68.3 | 82.4 | 84.0 | 84.4 | 78.4 | 74.4 |

TABLE 2

| | | Comp. Ex. 5 | Ex. 9 | Ex. 10 | Ex.11 | Ex. 12 | Comp. Ex. 6 | Comp. Ex. 7 | Ex. 13 | Ex. 14 | Ex. 15 | Ex. 16 | Comp. Ex. 8 |
|---|---|---|---|---|---|---|---|---|---|---|---|---|---|
| Composition of metallic element in | Ni (atomic %) | 70 | 70 | 70 | 70 | 70 | 70 | 80 | 80 | 80 | 80 | 80 | 80 |
| | Zr (atomic %) | 26.3 | 25.7 | 25.0 | 24.0 | 22.5 | 20.0 | 17.5 | 17.1 | 16.7 | 16.0 | 15.0 | 13.3 |
| | Ca (atomic %) | 3.8 | 4.3 | 5.0 | 6.0 | 7.5 | 10.0 | 2.5 | 2.9 | 3.3 | 4.0 | 5.0 | 6.7 |

TABLE 2-continued

| | | Comp. Ex. 5 | Ex. 9 | Ex. 10 | Ex. 11 | Ex. 12 | Comp. Ex. 6 | Comp. Ex. 7 | Ex. 13 | Ex. 14 | Ex. 15 | Ex. 16 | Comp. Ex. 8 |
|---|---|---|---|---|---|---|---|---|---|---|---|---|---|
| catalyst | Zr + Ca (atomic %) | 30 | 30 | 30 | 30 | 30 | 30 | 20 | 20 | 20 | 20 | 20 | 20 |
| | Ca/(Zr + Ca) | 0.125 | 0.143 | 0.167 | 0.200 | 0.250 | 0.333 | 0.125 | 0.143 | 0.167 | 0.200 | 0.250 | 0.333 |
| Lattice spacing d(nm) between [111] planes of Zr support | | 0.2945 | 0.2945 | 0.2947 | 0.2952 | 0.2953 | 0.2955 | — | — | — | — | — | — |
| $CO_2$ conversion ratio(%) | 300° C. | 15.3 | 23.7 | 42.4 | 47.9 | 39.1 | 27.7 | — | — | — | — | — | — |
| | 350° C. | 17.1 | 75.9 | 91.8 | 91.2 | 84.0 | 78.3 | 67.0 | 77.1 | 83.8 | 85.4 | 76.6 | 72.6 |
| | 400° C. | 74.0 | 79.8 | 85.2 | 85.2 | 85.1 | 81.7 | — | — | — | — | — | — |

TABLE 3

| | | Comp. Ex. 9 | Ex. 17 | Ex. 18 | Ex. 19 | Ex. 20 | Comp. Ex. 10 |
|---|---|---|---|---|---|---|---|
| Composition of metallic element in catalyst | Ni (atomic %) | 90 | 90 | 90 | 90 | 90 | 90 |
| | Zr (atomic %) | 8.8 | 8.6 | 8.3 | 8.0 | 7.5 | 6.7 |
| | Ca (atomic %) | 1.3 | 1.4 | 1.7 | 2.0 | 2.5 | 3.3 |
| | Zr + Ca (atomic %) | 10 | 10 | 10 | 10 | 10 | 10 |
| | Ca/(Zr + Ca) | 0.125 | 0.143 | 0.167 | 0.200 | 0.250 | 0.333 |
| Lattice spacing d(nm) between [111] planes of Zr support | | — | — | — | — | — | — |
| $CO_2$ conversion ratio(%) | 300° C. | — | — | — | — | — | — |
| | 350° C. | 65.9 | 71.7 | 70.4 | 74.4 | 73.5 | 72.2 |
| | 400° C. | — | — | — | — | — | — |

TABLE 4

| | | Comp. Ex. 11 | Ex. 21 | Ex. 22 | Ex. 23 | Ex. 24 | Comp. Ex. 12 |
|---|---|---|---|---|---|---|---|
| Composition of metallic element in catalyst | Ni (atomic %) | 50 | 50 | 50 | 50 | 50 | 50 |
| | Zr (atomic %) | 43.8 | 42.9 | 41.7 | 40.0 | 37.5 | 33.4 |
| | Ca (atomic %) | 6.3 | 7.2 | 8.4 | 10.0 | 12.5 | 16.7 |
| | Zr + Ca (atomic %) | 50 | 50 | 50 | 50 | 50 | 50 |
| | Ca/(Zr + Ca) | 0.125 | 0.143 | 0.167 | 0.200 | 0.250 | 0.333 |
| Lattice spacing d(nm) between Zr support [111] plane | | 0.2946 | 0.2950 | 0.2953 | 0.2954 | 0.2958 | 0.2961 |

While the illustrative embodiments of the present invention are provided in the above description, such is for illustrative purpose only and it is not to be construed as limiting in any manner Modification and variation of the present invention that will be obvious to those skilled in the art is to be covered by the following claims.

INDUSTRIAL APPLICABILITY

The methanation reaction catalyst and the method for producing methane of the present invention are suitably used for, for example, a carbon dioxide methanation system. The method for producing a methanation reaction catalyst of the present invention is suitably used for a method for producing a methanation reaction catalyst.

The invention claimed is:

1. A method for producing a methanation reaction catalyst and for producing methane using the methanation reaction catalyst, the method comprising producing the methanation reaction catalyst by:
   preparing a mixture by mixing zirconia and/or a Zr salt, a Ca salt, and a Ni salt so that based on the metals in the element state, the following atomic percent is achieved:
   Zr: 6 to 62 atomic %,
   Ca: 1 to 20 atomic %, and
   Ni: 30 to 90 atomic %, and that the atomic ratio of Ca/(Zr+Ca) is 0.14 to 0.25 and the atomic ratio of (Ca+Ni)/(Zr+Ca+Ni) is 0.740 to 0.90;
   calcining the mixture at 600 to 800° C.; and
   then reducing the calcined product,
   the method further comprising producing the methane by:
   contacting the methanation reaction catalyst with a gas mixture containing at least carbon dioxide and hydrogen gas under the conditions of 350 to 400° C.

* * * * *